US010400187B2

(12) United States Patent
Tanaka et al.

(10) Patent No.: US 10,400,187 B2
(45) Date of Patent: Sep. 3, 2019

(54) NATURAL GAS REFINING APPARATUS AND SYSTEM

(71) Applicant: MITSUBISHI HEAVY INDUSTRIES, LTD., Tokyo (JP)

(72) Inventors: Yukio Tanaka, Tokyo (JP); Ryuji Yoshiyama, Tokyo (JP); Masayuki Eda, Tokyo (JP); Tomoh Akiyama, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 198 days.

(21) Appl. No.: 15/533,260

(22) PCT Filed: Nov. 16, 2015

(86) PCT No.: PCT/JP2015/082072
§ 371 (c)(1),
(2) Date: Jun. 5, 2017

(87) PCT Pub. No.: WO2016/088538
PCT Pub. Date: Jun. 9, 2016

(65) Prior Publication Data
US 2017/0327758 A1    Nov. 16, 2017

(30) Foreign Application Priority Data

Dec. 4, 2014    (JP) .................................. 2014-245975

(51) Int. Cl.
*C10L 3/10* (2006.01)
*B01D 53/14* (2006.01)
(Continued)

(52) U.S. Cl.
CPC .............. *C10L 3/104* (2013.01); *B01D 53/14* (2013.01); *B01D 53/1475* (2013.01);
(Continued)

(58) Field of Classification Search
CPC ................ B01D 53/04; B01D 53/1425; B01D 53/1475; B01D 53/22; B01D 53/226;
(Continued)

(56) References Cited

U.S. PATENT DOCUMENTS 6,228,145 B1 *   5/2001   Falk-Pedersen ..... B01D 53/229
                                                          95/44
2007/0283813 A1 * 12/2007  Iijima ................. B01D 53/1425
                                                          96/235
(Continued)

FOREIGN PATENT DOCUMENTS

JP        H10-272333 A    10/1998
JP        2007-254572 A   10/2007
(Continued)

OTHER PUBLICATIONS

International Preliminary Report on Patentability issued in PCT/JP2015/082072 dated Jun. 6, 2017 (1 page).
(Continued)

*Primary Examiner* — Jason M Greene
(74) *Attorney, Agent, or Firm* — Osha Liang LLP

(57) ABSTRACT

A natural gas refining apparatus including a first separation membrane unit including a first separation membrane; and a second separation membrane unit provided in a subsequent stage of the first separation membrane unit. The second separation membrane unit includes a second separation membrane that allows an amine solution to circulate through the second separation membrane unit, and the natural gas refining apparatus refines raw natural gas containing $CO_2$ by passing the raw natural gas through the first and second separation membrane units, separating $CO_2$-rich gas with the first and second separation membranes, and absorbing $CO_2$ with the amine solution circulating through the second separation membrane unit.

4 Claims, 8 Drawing Sheets

(51) Int. Cl.
*B01D 53/18* (2006.01)
*B01D 53/22* (2006.01)
*C07C 7/11* (2006.01)
*C07C 7/00* (2006.01)
*C07C 7/144* (2006.01)
*C01B 32/50* (2017.01)
*C07C 9/04* (2006.01)
*B01D 53/00* (2006.01)
*B01D 53/047* (2006.01)
*B01D 71/02* (2006.01)
*B01D 69/02* (2006.01)

(52) U.S. Cl.
CPC ............ *B01D 53/18* (2013.01); *B01D 53/22* (2013.01); *B01D 53/229* (2013.01); *B01D 69/02* (2013.01); *B01D 71/02* (2013.01); *C07C 7/005* (2013.01); *C07C 7/11* (2013.01); *C07C 7/144* (2013.01); *C10L 3/103* (2013.01); *B01D 53/002* (2013.01); *B01D 53/047* (2013.01); *B01D 53/226* (2013.01); *B01D 53/227* (2013.01); *B01D 2252/20484* (2013.01); *B01D 2256/245* (2013.01); *B01D 2257/504* (2013.01); *B01D 2325/20* (2013.01); *C01B 32/50* (2017.08); *C07C 9/04* (2013.01); *C10L 2290/10* (2013.01); *C10L 2290/12* (2013.01); *C10L 2290/542* (2013.01); *C10L 2290/548* (2013.01); *Y02C 10/06* (2013.01); *Y02C 10/10* (2013.01); *Y02P 20/152* (2015.11)

(58) Field of Classification Search
CPC .... B01D 53/228; B01D 53/229; B01D 63/02; B01D 63/06; B01D 71/02; B01D 71/028; B01D 2256/245; B01D 2257/504; B01D 2325/20; C07C 7/11; C07C 7/144; C10L 3/104

See application file for complete search history.

(56) References Cited

U.S. PATENT DOCUMENTS

| | | | |
|---|---|---|---|
| 2008/0011161 A1* | 1/2008 | Finkenrath | B01D 53/229 96/4 |
| 2008/0216650 A1* | 9/2008 | Falconer | B01D 71/028 95/51 |
| 2010/0116130 A1* | 5/2010 | Carreon | B01D 71/028 95/45 |
| 2012/0111051 A1 | 5/2012 | Kulkarni et al. | |
| 2012/0111192 A1* | 5/2012 | Nazarko | B01D 53/229 95/51 |
| 2013/0213086 A1 | 8/2013 | Maher | |
| 2013/0324397 A1* | 12/2013 | Wilson | B01D 53/04 502/416 |
| 2014/0134695 A1* | 5/2014 | Zhou | B01D 53/1406 435/167 |
| 2014/0144321 A1* | 5/2014 | Sawamura | B01D 53/229 96/4 |
| 2014/0360938 A1* | 12/2014 | Hayashi | B01D 71/028 210/638 |
| 2015/0122122 A1* | 5/2015 | W Mustapa | B01D 53/229 95/51 |

FOREIGN PATENT DOCUMENTS

| | | |
|---|---|---|
| JP | 2013-226534 A | 11/2013 |
| WO | 2012/153808 A1 | 11/2012 |
| WO | 2013/125660 A1 | 8/2013 |

OTHER PUBLICATIONS

Written Opinion of the International Searching Authority issued in PCT/JP2015/082072 dated Jan. 26, 2016, with English translation thereof (14 pages).

International Search Report issued in corresponding International Application No. PCT/JP2015/082072 dated Jan. 26, 2016, with English translation thereof (9 pages).

* cited by examiner

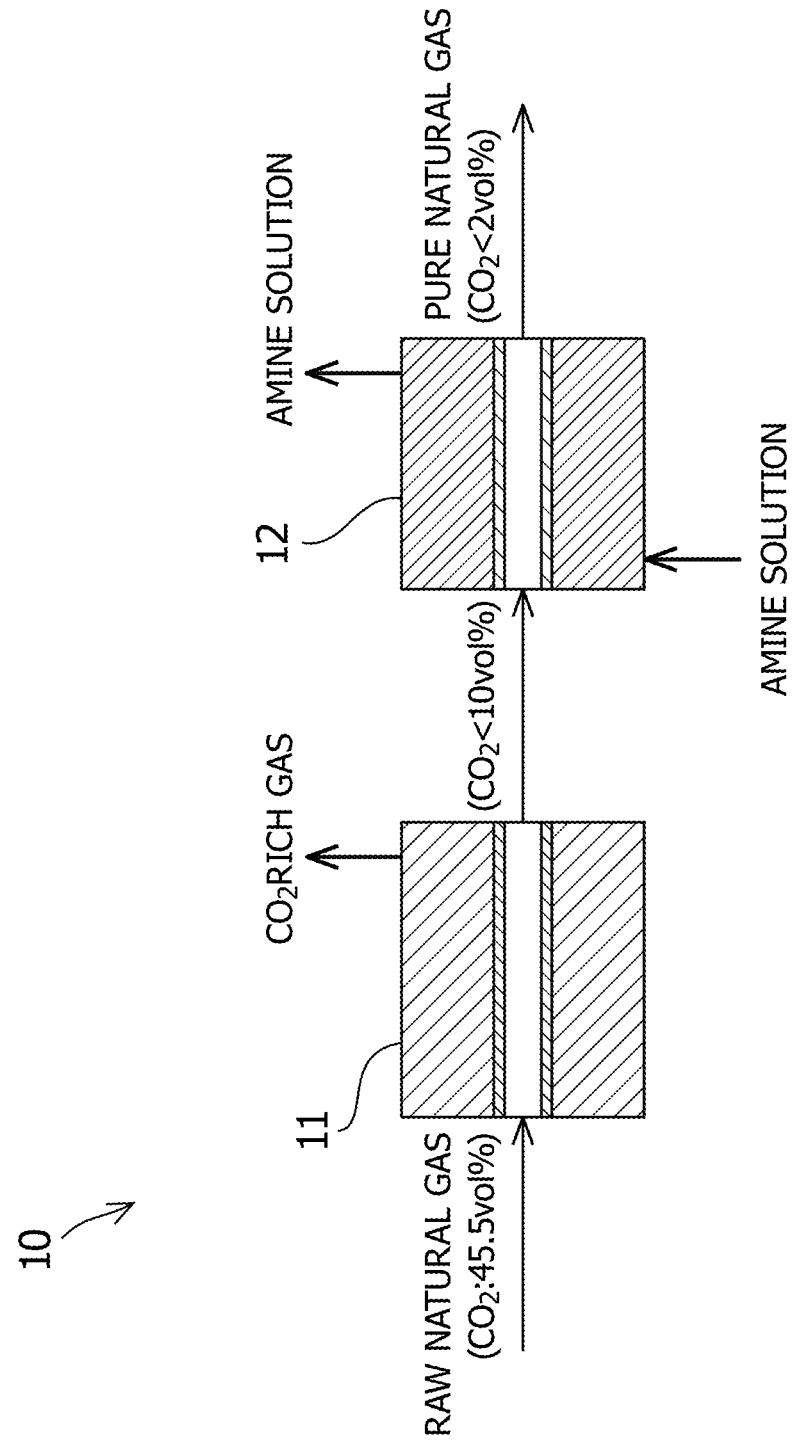

NATURAL GAS REFINING APPARATUS AND SYSTEM

TECHNICAL FIELD

One or more embodiments of the present invention relate to a natural gas refining apparatus and system, and particularly relates to a natural gas refining apparatus and system to purify natural gas from $CO_2$-rich acid gas such as associated gas.

BACKGROUND

Natural gas coming from below the surface of the earth has contained associated gas which accompanies the production. Such associated gas contains acid gas containing $CO_2$, that is, gas with greenhouse effects. For this reason, in a natural gas refinery plant, $CO_2$ is separated and recovered from the natural gas, and the purified gas is delivered as pure natural gas to a process to produce final salable products.

As such a purification process, a process has been disclosed which includes: after removing water from raw natural gas, performing cryogenic separation by compressing and cooling to recover $CO_2$-rich gas as liquefied carbonic acid gas; further compressing hydrocarbon rich gas from which $CO_2$ is removed; and performing membrane separation with a polymer separation membrane to recover pure natural gas having a $CO_2$ concentration of 10% by volume or less (Patent Literature 1).

In addition, a process has been also disclosed which includes: after removing water from raw natural gas, performing membrane separation with a polymer separation membrane in a first stage, followed by cryogenic separation with compressing and cooling to recover $CO_2$-rich gas as liquefied carbonic acid gas; and further using $CH_4$-rich gas, from which $CO_2$ is removed, as sweep gas for membrane separation in a second stage (Patent Literature 2). In Patent Literatures 1 and 2, the $CO_2$-rich gas permeated through the separation membrane is circulated to the cryogenic separation or the membrane separation in the preceding stage.

In order to achieve pure natural gas with required product quality (for example, a $CO_2$ concentration of 2% by volume or less), however, an example such as the aforementioned ones requires a huge membrane area, and therefore an apparatus and a system may have structures large in scale, and accordingly consume enormous amounts of energy. For this reason, in reality, $CO_2$ is separated by membrane separation using a membrane area smaller than necessary, and thereafter the $CO_2$ concentration is reduced to product quality by an additional process.

CITATION LIST

Patent Literatures

[Patent Literature 1] U.S. Patent Publication No. 2013-0213086
[Patent Literature 2] U.S. Patent Publication No. 2012-0111051

SUMMARY

One or more embodiments of the present invention provide a natural gas refining apparatus and system that are made compact in structure to reduce energy consumption, and that are capable of purifying natural gas with favorable quality.

According to one or more embodiments of the present invention, a first separation membrane unit including a separation membrane and a second separation membrane unit provided in a subsequent stage of the first separation membrane unit, including a separation membrane, allow an amine solution to circulate through the second separation membrane unit. The natural gas refining apparatus refines raw natural gas containing $CO_2$ by passing the raw natural gas through the first and second separation membrane units, thereby separating $CO_2$-rich gas with the separation membranes and absorbing $CO_2$ with the amine solution circulating through the second separation membrane unit.

With this structure, the amine solution for absorbing $CO_2$ is circulated on a secondary side of the second separation membrane unit, so that the $CO_2$ in the raw natural gas is separated, absorbed and thereby recovered, and that a $CO_2$ partial pressure on the secondary side of the second separation membrane unit is reduced to ensure a $CO_2$ partial pressure difference (driving force) between the front and back sides of the separation membrane. As a result, the membrane area in the natural gas refining apparatus can be reduced. Moreover, the equipment cost or the running cost of the apparatus can be reduced by changing, as needed, the load or the membrane area required for the first and/or second separation membrane unit.

In the specification and claims of the present application, raw natural gas is associated gas or the like, and is natural gas before purification which contains hydrocarbons such as methane ($CH_4$), carbon dioxide ($CO_2$), hydrogen disulfide ($H_2S$), and the like. In addition, of the front and back sides of a separation membrane, a side fed with a fluid such as natural gas is referred to as a primary side of the apparatus or the separation membrane, and the back side of the former side is referred to as a secondary side thereof. Then, an upstream side of a flow of the fluid is referred to as a preceding stage, and a downstream side of the flow is referred to as a subsequent stage.

Moreover, the first and second separation membrane units may each have a $CO_2/CH_4$ selectivity of 100 or more, and have a permeation coefficient value of $1.0 \times 10^{-3}$ Ncc/($cm^2 \cdot s \cdot cmHg$) or more.

This structure makes it possible to significantly reduce the membrane area in the natural gas refining apparatus, and to obtain pure natural gas with product quality purified to a $CO_2$ concentration of 2% by volume or less. In the specification and claims of the present application, the $CO_2/CH_4$ selectivity means a $CO_2$ concentration on the secondary side/a $CH_4$ concentration on the secondary side under the condition that a $CO_2$ concentration on the primary side is 50%.

One or more embodiments of the present invention provide for a natural gas refining system. This natural gas refining system includes the above natural gas refining apparatus, and a regeneration tower configured to separate and recover $CO_2$ from the amine solution after circulating through the second separation membrane unit to regenerate the $CO_2$, and send the recovered $CO_2$ to the $CO_2$-rich gas separated with the separation membrane.

The system having the above structure is capable of separating, in the system, $CO_2$ absorbed by the amine solution circulating through the second separation membrane unit, joining the separated $CO_2$ into the $CO_2$-rich gas permeated through the natural gas refining apparatus, and thereby efficiently recovering the resultant $CO_2$-rich gas as liquefied carbonic acid gas.

In another configuration, a natural gas refining system according to one or more embodiments of the present invention may have a structure further including a gas-liquid separator configured to recover, as liquefied carbonic acid gas, the $CO_2$-rich gas permeated through the first separation membrane unit, separate $CH_4$-rich gas from the $CO_2$-rich gas, and send the separated $CH_4$-rich gas back to a preceding stage of the second separation membrane unit.

With this configuration, it is possible to separate $CO_2$ from the $CO_2$-rich gas permeated through the natural gas refining apparatus to increase the concentration, and to recover the $CO_2$ as liquefied carbonic acid gas. It is also possible to separate $CH_4$ contained in the $CO_2$-rich gas and efficiently recycle the $CH_4$ by sending the $CH_4$ back to the natural gas refining apparatus.

In another configuration, a natural gas refining system according to one or more embodiments of the present invention may have a structure further including a $H_2S$ adsorption tower provided in a preceding stage of the natural gas refining apparatus and configured to adsorb $H_2S$ in the raw natural gas and desorb and recover the adsorbed $H_2S$.

With this configuration, the $H_2S$ concentration in the raw natural gas is reduced in the preceding stage of the natural gas refining apparatus, so that the $H_2S$ in the gas can be prevented from deteriorating the separation membranes, and a thermostable amine salt, which may be produced by a reaction of the $H_2S$ with the amine solution, can be prevented from lowering the $CO_2$ absorption efficiency of the amine solution.

According to one or more embodiments of the present invention a natural gas refining apparatus and system are made compact in structure to reduce energy consumption, and are capable of purifying natural gas with favorable quality.

BRIEF DESCRIPTION OF DRAWINGS

FIG. 1 is a conceptual diagram for explaining an outline for an embodiment of a natural gas refining apparatus according to one or more embodiments of the present invention.

DESCRIPTION OF EMBODIMENTS

Figure 2A:
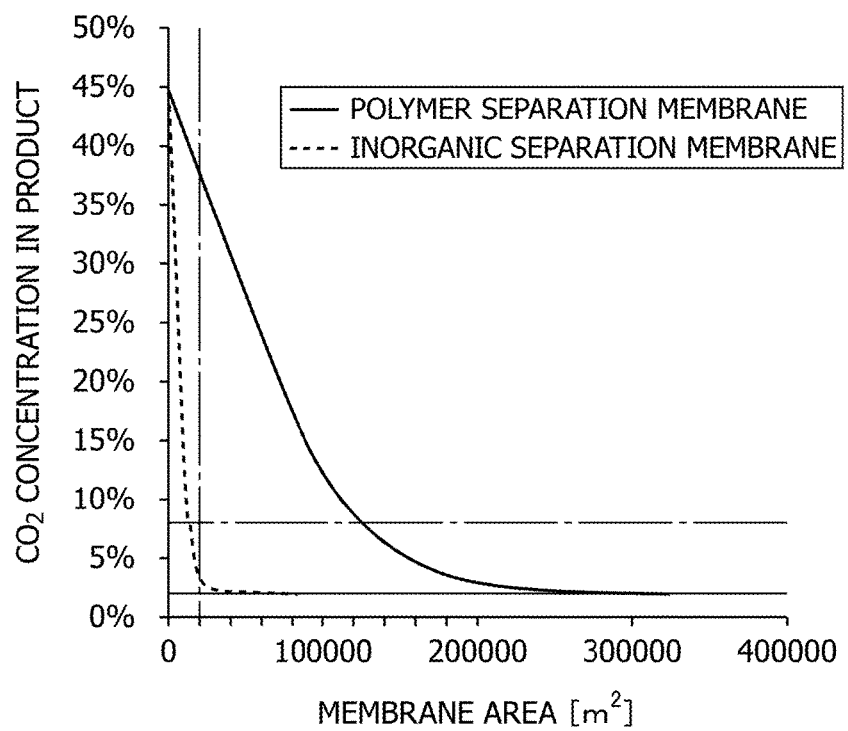
FIGS. 2A and 2B are graphs for explaining an effect of a natural gas refining apparatus and system according to one or more embodiments of the present invention.

Hereinafter, a natural gas refining apparatus and system according to one or more embodiments of the present invention are described in detail with reference to the accompanying drawings.

[Natural Gas Refining Apparatus]

FIG. 1 conceptually shows a natural gas refining apparatus according to one or more embodiments of the present invention. A natural gas refining apparatus 10 includes at least a first separation membrane unit 11 and a second separation membrane unit 12. The first and second separation membrane units 11, 12 are coupled to each other with an airtight member, such as a pipe, for example, through which natural gas containing at least hydrocarbons such as $CH_4$ and $CO_2$ can flow.

The first separation membrane unit 11 is provided in a preceding stage inside the natural gas refining apparatus 10, feeds raw natural gas to a separation membrane to separate, as $CO_2$-rich gas, $CO_2$ permeated through the separation membrane, and thereby allows $CH_4$-rich gas with a $CO_2$ concentration thus reduced to pass through the first separation membrane unit 11. The gas flowing from the first separation membrane unit 11 is further fed to the second separation membrane unit 12 provided in the subsequent stage thereof. An amine solution circulates as a sweep solution on a secondary side of a separation membrane inside the second separation membrane unit 12. This amine solution absorbs $CO_2$ permeated through the separation membrane, and reduces a $CO_2$ partial pressure on the secondary side of the separation membrane of the second separation membrane unit 12 to ensure a $CO_2$ partial pressure difference between the front and back sides of the separation membrane. As a result, the membrane area necessary to refine the raw natural gas to the product quality can be made small.

The raw natural gas containing $CO_2$ is run through the natural gas refining apparatus 10, so that the $CO_2$-rich gas permeated through the separation membrane of the first separation membrane unit 11 is recovered, and that the $CO_2$ permeated through the separation membrane of the second separation membrane unit 12 is absorbed by the amine solution. As shown in FIG. 1, in the case of raw natural gas having a $CO_2$ concentration of 45.5% by volume, for example, the $CO_2$ concentration can be reduced to 10% by volume or less by the permeation through the first separation membrane unit 11, and then can be further reduced to 2% by volume or less by the permeation through the subsequent second separation membrane unit 12.

The first separation membrane unit 11 is not particularly limited, but may be equipped with a separation membrane having a $CO_2/CH_4$ selectivity of 100 or more and a permeation coefficient value of $1.0 \times 10^{-3}$ Ncc/(cm$^2$·s·cmHg) or more. As such a separation membrane, there is an inorganic separation membrane made of zeolite of DDR type, CHA type or the like expressed by specification codes defined by the International Zeolite Association (IZA), for example. In this case, from the practical viewpoint, the membrane area of the natural gas refining apparatus 10 can be further reduced as compared with a case using a polymer separation membrane.

The second separation membrane unit 12 is equipped with the separation membrane to separate $CO_2$, and allows an amine solution fed from outside to circulate as a sweep solution inside the second separation membrane unit 12. The separation membrane of the second separation membrane unit 12 may be the same as the separation membrane of the first separation membrane unit 11. Moreover, the amine solution circulating through the second separation membrane unit 12 may be any sweep solution not particularly limited but being capable of absorbing at least $CO_2$. As such an amine solution, there are monoethanol amine (MEA), sterically hindered amines KS-1 (registered trademark), KS-2 (registered trademark), KS-3 (registered trademark), and the like.

Effects of the present embodiment are further described with reference to FIGS. 2(*a*) and 2(*b*).

FIG. 2A shows an estimation result of a change in the $CO_2$ concentration (% by volume) with respect to the membrane area ($m^2$) of each of the separation membrane units, which is based on assumed performance of a separation membrane unit including a typical polymer separation membrane and assumed performance of a separation membrane unit including a typical inorganic separation membrane. Receiving conditions such as a volume of gas to be treated, pressure, and a ratio of $CO_2:CH_4$ are the same for both the separation membrane units, and the $CO_2/CH_4$ selectivity of the polymer and inorganic separation membranes is 30 for the polymer separation membrane, and 100 for the inorganic separation membrane. Moreover, the permeation coefficient of the polymer separation membrane is $0.10 \times 10^{-3}$ Ncc/($cm^2 \cdot s \cdot cmHg$), and the permeation coefficient of the inorganic separation membrane is $1.0 \times 10^{-3}$ Ncc/($cm^2 \cdot s \cdot cmHg$).

As shown in FIG. 2A, in the case of the separation membrane unit employing the typical polymer separation membrane, the membrane area for achieving a $CO_2$ concentration of 8% by volume or less is about 130,000 $m^2$, and the membrane area for achieving a $CO_2$ concentration of 2% by volume or less is about 300,000 $m^2$. In contrast to this, in the case of the separation membrane unit 11 employing the typical inorganic separation membrane, the membrane area for achieving a $CO_2$ concentration of 8% by volume or less is about 12,000 $m^2$, and the membrane area for achieving a $CO_2$ concentration of 2% by volume or less is about 80,000 $m^2$. Thus, it can be seen that the first separation membrane unit 11 employing the typical inorganic separation membrane can achieve a significant reduction in the membrane area for obtaining pure natural gas with required product quality.

Figure 2B:
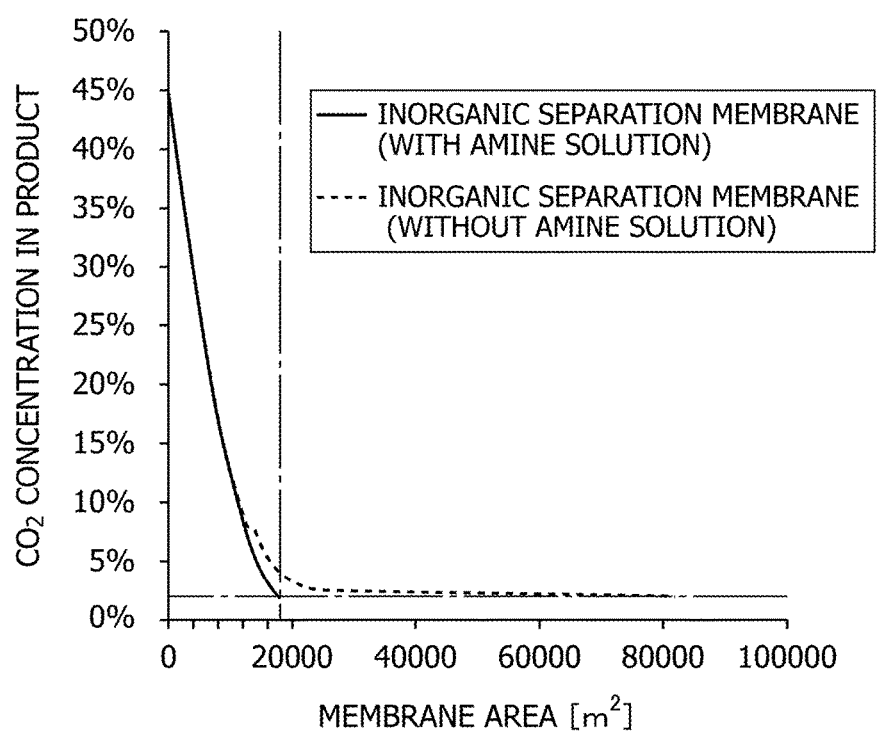

In addition, FIG. 2B shows an estimation result of a change in the $CO_2$ concentration (% by volume) with respect to the membrane area ($m^2$), which is based on assumed performance of a natural gas refining apparatus equipped with the first separation membrane unit 11 including a typical inorganic separation membrane and assumed performance of the natural gas refining apparatus 10 equipped with the first and second separation membrane units 11, 12 each including a typical inorganic separation membrane. The receiving conditions for both the natural gas refining apparatuses, and the $CO_2/CH_4$ selectivity and the permeation coefficient of the inorganic separation membranes are the same as the conditions shown in FIG. 2A. As shown in FIG. 2B, in the case of the natural gas refining apparatus equipped with only the separation membrane unit 11, the membrane area for achieving a $CO_2$ concentration of 2% by volume or less is about 80,000 $m^2$. In contrast to this, in the case of the natural gas refining apparatus 10 equipped with both the separation membrane units 11, 12, the membrane area for achieving a $CO_2$ concentration of 2% by volume or less is about 18,000 $m^2$. Thus, it can be seen that the natural gas refining apparatus 10 further equipped with the second separation membrane unit 12 can reduce more the membrane area for obtaining pure natural gas with required product quality than otherwise.

As described above, according to the present embodiment, the amine solution circulating through the second separation membrane unit 12 can reduce the $CO_2$ partial pressure on the secondary side of the second separation membrane unit 12. This ensures a $CO_2$ partial pressure difference (driving force) between the front and back sides of the separation membrane in the second separation membrane unit 12, and thereby ensures a permeation speed of the gas passing through the first and second separation membrane units 11, 12. Hence, even if the $CO_2$ partial pressure of the gas passing on the primary side of the natural gas refining apparatus is reduced, the membrane area of the separation membrane does not have to be increased, and accordingly the membrane area of the natural gas refining apparatus can be reduced significantly. Moreover, the apparatus can be made compact and the easiness of operations of the apparatus can be improved. In addition, according to the present embodiment, it is possible to reduce the equipment cost or the running cost by changing, as needed, the load or the membrane area required for the first and/or second separation membrane unit 11, 12. The load is, for example, a permeate volume of $CO_2$ in the first separation membrane unit 11 or the second separation membrane unit 12. For example, if the permeate volume of $CO_2$ in the first separation membrane unit 11 is increased, the running cost can be saved. On the other hand, if the permeate volume of $CO_2$ in the second separation membrane unit 12 is reduced, the equipment cost can be saved. Instead, for example, if the membrane area of the first separation membrane unit 11 is increased, the running cost such as energy cost can be reduced, whereas if the membrane area of the second separation membrane unit 12 is increased, the equipment cost for the first separation membrane unit 11 and the like can be reduced.

Figure 3:
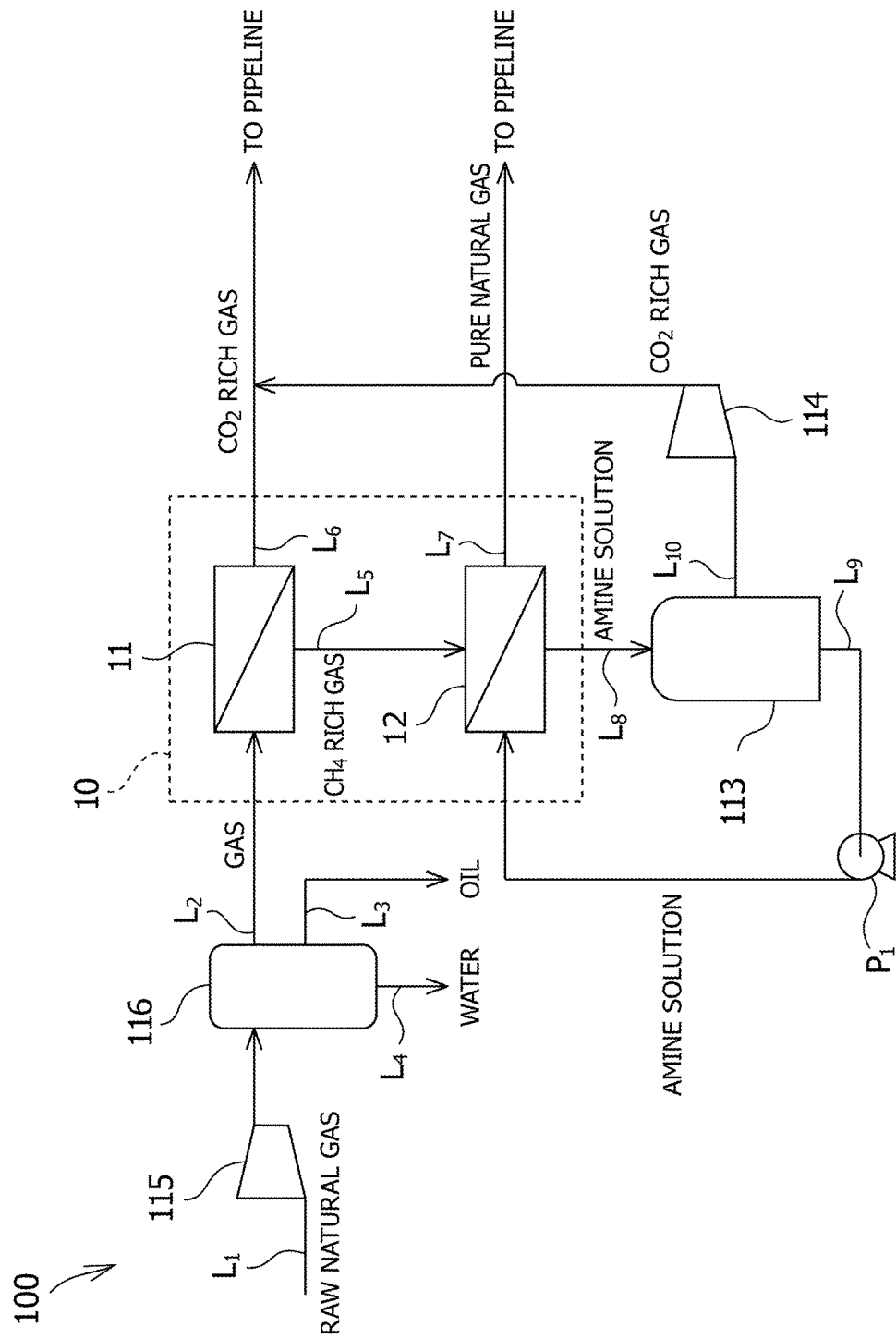
FIG. 3 is a conceptual diagram for explaining an outline for a first embodiment of a natural gas refining system according to one or more embodiments of the present invention.

With reference to FIG. 3, description is provided for a first embodiment of a natural gas refining system equipped with the natural gas refining apparatus 10 with the aforementioned structure. A natural gas refining system 100 includes at least a regeneration tower 113, compressors 114, 115, and a gas-liquid separator 116 in addition to the natural gas refining apparatus 10.

The regeneration tower 113 is a tower that heats the amine solution containing absorbed $CO_2$ and sent out from the second separation membrane unit 12 through a line $L_8$ to thereby separate and recover the $CO_2$ from the amine solution, and recirculates the $CO_2$-released amine solution to the second separation membrane unit 12 through a line $L_9$ and a pump $P_1$. Meanwhile, the $CO_2$-rich gas permeated through the first separation membrane unit 11 is recovered through a line $L_6$. The $CO_2$-rich gas separated and recovered by the regeneration tower 113 flows from a line $L_{10}$ through the compressor 114 and also joins into the gas in the line $L_6$. Incidentally, the $CO_2$-rich gas in the line $L_6$ may be further compressed depending on use by a compressor (not shown).

In the natural gas refining system 100, the compressor 115 in a line $L_1$ raises the pressure of the raw natural gas, and then sends the raw natural gas to the gas-liquid separator 116. The gas-liquid separator 116 separates, from the raw natural gas, water in a liquid phase and oil for liquefied natural gas (LNG) containing hydrocarbons having 2 to 5 carbon atoms, recovers the oil and the water through lines $L_3$ and $L_4$, respectively, and sends the residue gas in a gaseous phase from which the water and the oil are removed to the natural gas refining apparatus 10 through a line $L_2$. In this way, the LNG component is recovered in the preceding stage of the natural gas refining apparatus 10, and the $CO_2$ in the liquid phase is recovered in the subsequent stage. Incidentally, in the case in which the raw natural gas has a high water content, for example, the water content is 50 ppm or more, a dehydrator (not shown) may be optionally provided to the line $L_2$, and may dehydrate the gas to a water content suitable for purification of the natural gas.

According to the present embodiment, the $CO_2$ absorbed by the amine solution on the secondary side of the separation membrane of the second separation membrane unit 12 is separated and recovered in the regeneration tower 113, and then the recovered $CO_2$ is joined to the $CO_2$-rich gas permeated through the natural gas refining apparatus 10, so that the liquefied carbonic acid gas can be recovered with high efficiency. Moreover, the amine solution from which the $CO_2$ is removed is recirculated as a regenerated amine solution to the second separation membrane unit 12, and thus is recycled. Further, as in the first embodiment, the equipment cost for the system and the running cost for regeneration of the absorbent solution and the like can be reduced by changing, as needed, the membrane area or the load required for the first and/or second separation membrane unit 11, 12. Furthermore, the system can be also made compact and improved in the easiness of operations.

Figure 4:
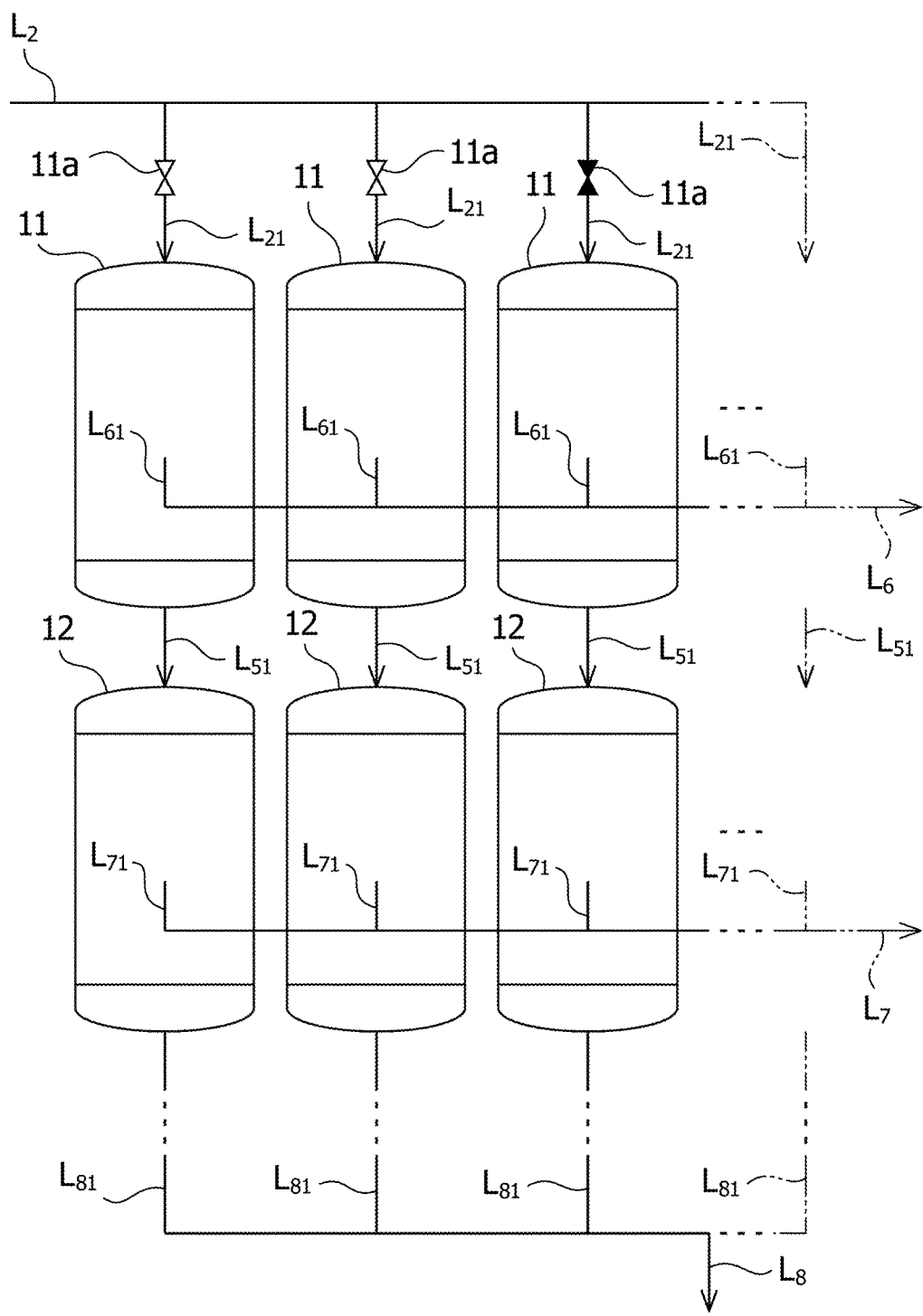
FIG. 4 is a conceptual diagram for explaining a more specific configuration of a natural gas refining apparatus applied to a natural gas refining system according to one or more embodiments of the present invention.

As shown in FIG. 4, more detailed description is provided for a more specific configuration of the aforementioned separation membrane units 11, 12 in terms of a layout and the numbers of these units. As shown in FIG. 4, from the practical viewpoint, two or more first separation membrane units 11 and two or more second separation membrane units 12 may be arranged in series or in parallel in a flow direction of raw natural gas.

First, two or more pairs of first separation membrane units 11 and second separation membrane units 12 may be arranged in series between the line $L_2$ and the line $L_8$ depending on the required product quality. When the two or more pairs of separation membrane units are arranged in series, a flow velocity of gas passing can be kept approximately at a predetermined level, and thereby the performance of the apparatus can be improved to satisfy the required product quality. The number of separation membrane units arranged in series may be determined depending on the flow velocity and the required product quality. The flow velocity is 0.1 m/s or more, and may be 1 m/s or more.

Two or more first separation membrane units 11 and two or more second separation membrane units 12 may be arranged in parallel between the line $L_2$ and the line $L_8$ depending on the capacities of the separation membrane units 11, 12. When the two or more separation membrane units are arranged in parallel, backup units having the same structure as that of the separation membrane units can be provided. Thus, use of the backup units enables the separation membrane units deteriorated in performance to be replaced without stopping the apparatus and/or the system. For example, in FIG. 4, one of on-off valves 11a provided to two or more lines $L_{21}$ branched from the line $L_2$ is closed to stop a flow of the raw natural gas to the corresponding one series of separation membrane units 11, 12 coupled in the series direction. The on-off valves 11a may be manual valves or automatic on-off valves. The separation membranes of the separation membrane units deteriorated in performance may be replaced while the separation membrane units for which the on-off valves 11a are not closed are operating. The backup units may be provided beforehand and set on standby. Then, the backup units may be switched from the separation membrane units deteriorated in performance, or may operate or stop operating with an increase or decrease in the volume of gas to be treated. The separation membrane units thus stopped may be subjected to treatment for reuse as needed such as replacement of a component. The $CO_2$-rich gas separated by the separation membrane units 11, 12 in operation is discharged from lines $L_{61}$, $L_{71}$ serving as permeate gas headers through the lines $L_6$, $L_7$. Meanwhile, the $CH_4$-rich gas flowing from the separation membranes of the separation membrane units 11, 12 is discharged through lines $L_{51}$, $L_{81}$, and $L_8$. The number of separation membrane units arranged in parallel may be determined depending on a volume of gas to be treated.

Figure 5A:
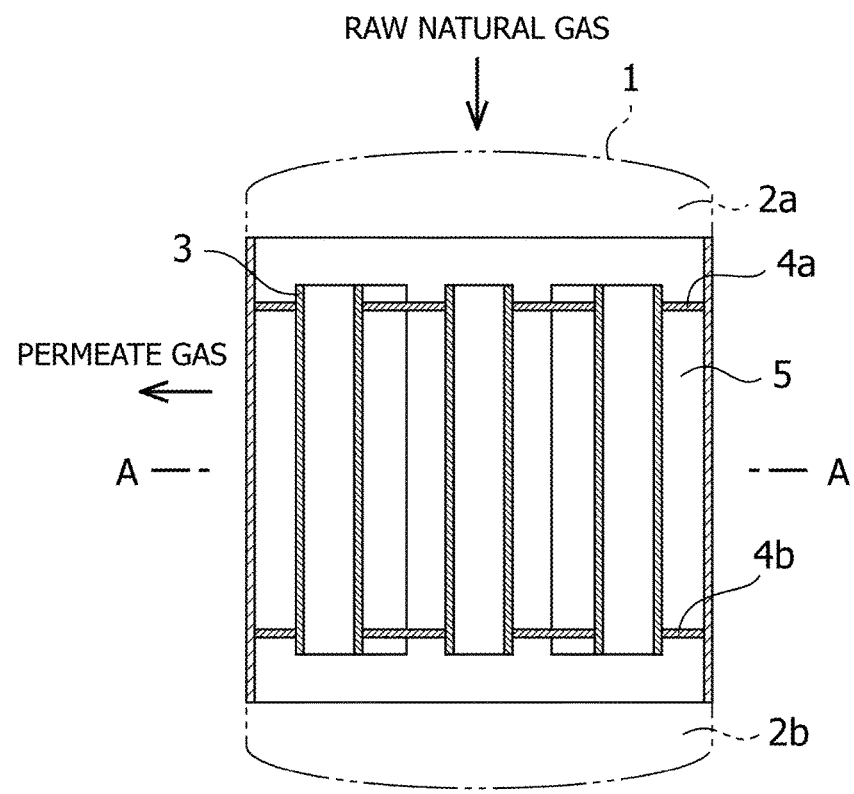
FIG. 5A is a conceptual diagram for explaining a more specific configuration of a separation membrane unit applied to a natural gas refining system and a natural gas refining apparatus according to one or more embodiments of the present invention.
Figure 5B:
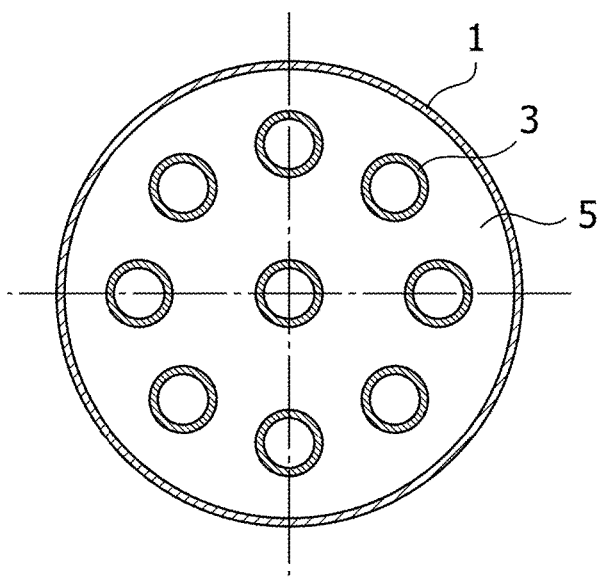
FIG. 5B is a cross sectional diagram of the separation membrane unit taken along a line A-A.

As shown in FIGS. 5A and 5B, a more specific configuration of the aforementioned separation membrane units 11, 12 is described in more detail. FIG. 5A is a schematic diagram showing a structure of a separation membrane unit to which a natural gas refining apparatus according to one or more embodiments of the present invention is applied, and FIG. 5B is a cross sectional diagram of the separation membrane unit taken along a line A-A.

As shown in FIG. 5A, the separation membrane unit employable as the separation membrane units 11, 12 may have a configuration where multiple pipe-form separation membranes 3 are stored in a vessel 1. The raw natural gas flows from an inlet (not-shown) into an upper channel 2a delimited by an outer wall of the vessel 1 and a pipe plate 4a and enters the primary sides of the separation membranes 3, in other words, inside the pipes of the separation membranes 3. Then, while the raw natural gas is passing on the primary sides of the separation membranes 3, the $CO_2$ contained in the raw natural gas permeates from the primary sides to the secondary side of the separation membranes 3. Thus, the raw natural gas is separated into $CO_2$-rich gas and $CH_4$-rich gas mainly containing $CH_4$. The $CH_4$-rich gas flows through a lower channel 2b delimited by the outer wall of the vessel 1 and a pipe plate 4b, and is discharged to a line from an outlet (not shown). Meanwhile, the $CO_2$ separated from the raw natural gas flows through an inner chamber 5 defined by outer sides of the separation membranes 3, the outer wall 1, and the pipe plates 4a, 4b and having at least air-tightness, and then is discharged to a line through an outlet channel (not shown). In the case in which the separation membrane unit 12 employs the separation membrane unit, the inner chamber 5 has both air-tightness and water-tightness, and the amine solution circulates through the inner chamber 5 from and to inlet and outlet channels (not shown).

As shown in FIG. 5B, nine separation membranes 3 are arranged in the vessel 1 in the present embodiment. The number of separation membranes 3 stored in the vessel 1 is not particularly limited to the above number. Then, the separation membranes 3 are arranged at positions at approximately equal intervals and point-symmetric to each other with respect to the center of the cross section of the vessel 1. This arrangement enables efficient operations of separating $CO_2$ by the separation membranes 3, circulating the $CO_2$ inside the inner chamber 5, and absorbing the $CO_2$ by the amine solution in the inner chamber 5. However, the positions of the separation membranes 3 in the vessel 1 are not particularly limited to the above, as a matter of course.

Figure 6:
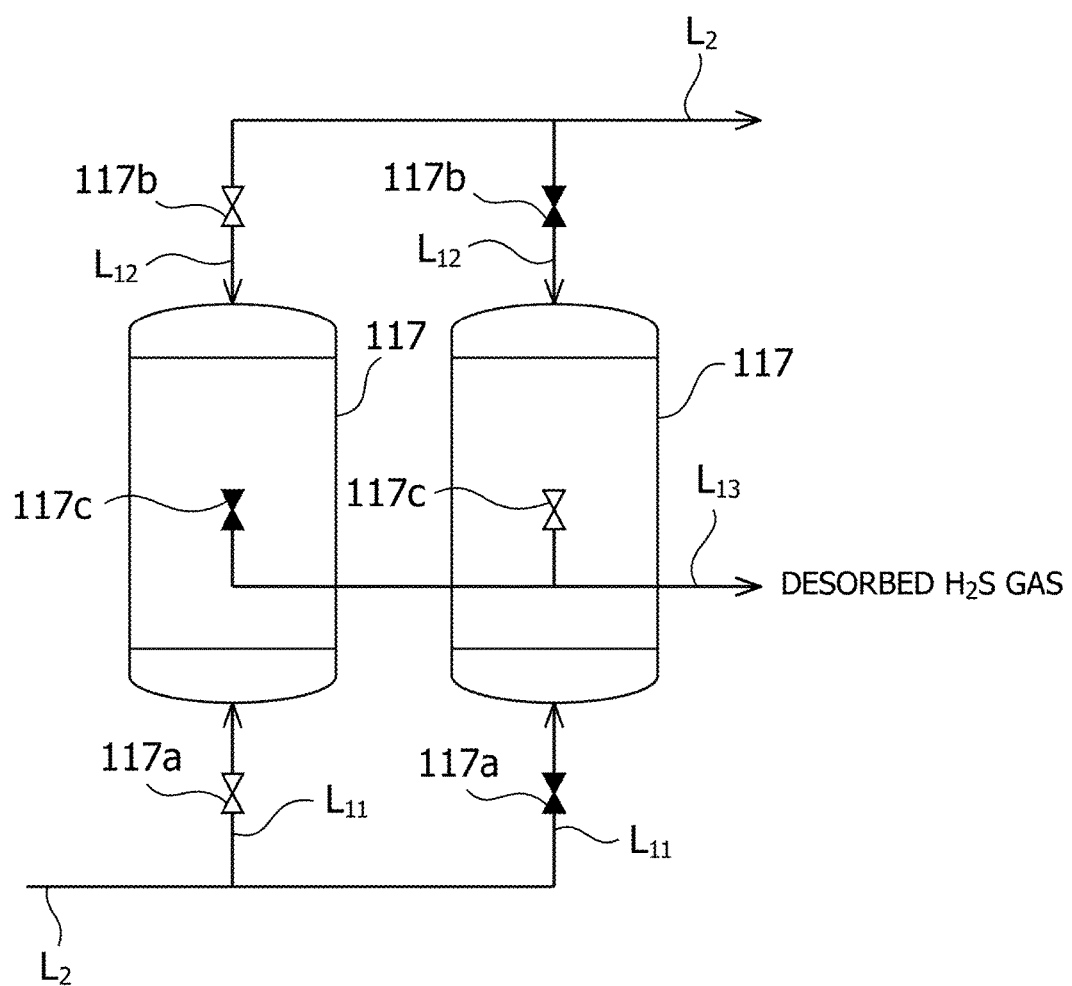
FIG. 6 is a conceptual diagram for explaining an outline for a $H_2S$ adsorption tower applied to a natural gas refining system according to one or more embodiments of the present invention.

Further, the natural gas refining system 100 (FIG. 3) according to the first embodiment may have a structure including a $H_2S$ adsorption tower 117 shown in FIG. 6.

A configuration shown in FIG. 6 includes two $H_2S$ adsorption towers 117, 117 in each of which a $H_2S$ adsorbent to adsorb $H_2S$ in the raw natural gas is provided. The two $H_2S$ adsorption towers 117, 117 are arranged in parallel, and each include on-off valves 117a to 117c. The on-off valves 117a to 117c may be manual valves or automatic on-off valves. In the present embodiment, the two adsorption towers 117 are provided, one of which is for adsorbing $H_2S$ and the other of which is for desorbing and recovering $H_2S$. Thereby, in the system in operation, the adsorption of $H_2S$ from the raw natural gas and the regeneration of the $H_2S$ adsorbent are simultaneously performed. With the on-off valves 117a, 117b opened and the on-off valve 117c closed, one of the adsorption towers 117 allows the raw natural gas to flow therethrough via both the lines $L_{11}$ and $L_{12}$, thereby adsorbing $H_2S$ with the $H_2S$ adsorbent and reducing the $H_2S$ concentration in the raw natural gas. At the same time, with the on-off valves 117a, 117b closed and the on-off valve 117c opened, the other adsorption tower 117 desorbs the $H_2S$ from the $H_2S$ adsorbent, thereby recovering the $H_2S$ as desorbed $H_2S$ gas through a line $L_{13}$ and regenerating the $H_2S$ adsorbent. The adsorption tower 117 in which the $H_2S$ adsorbent is regenerated can be used as the adsorption tower 117 for adsorbing $H_2S$. The number of adsorption towers 117 provided is not particularly limited but may be at least one. If two or more adsorption towers 117 are provided, at least one adsorption tower for desorbing and recovering $H_2S$ can be provided, and therefore the system can adsorb the $H_2S$ in the raw natural gas continuously without being stopped.

In such a configuration, the $H_2S$ concentration in the raw natural gas can be reduced in a preceding stage of the natural gas refining apparatus 10. This enables prevention of deterioration of the separation membranes in the natural gas refining apparatus 10 due to $H_2S$ contained in the raw natural gas. Thus, the performance of the natural gas refining apparatus 10 including the first and second separation membrane units 11, 12 and accordingly the performance of the natural gas refining system including the natural gas refining apparatus 10 can be prevented from being lowered due to the presence of $H_2S$. In addition, this also prevents a thermostable amine salt, which may be produced by a reaction of $H_2S$ with the amine solution, from lowering the $CO_2$ absorption efficiency of the amine solution in the second separation membrane unit 12 and the regeneration efficiency in the regeneration tower 113.

Figure 7:
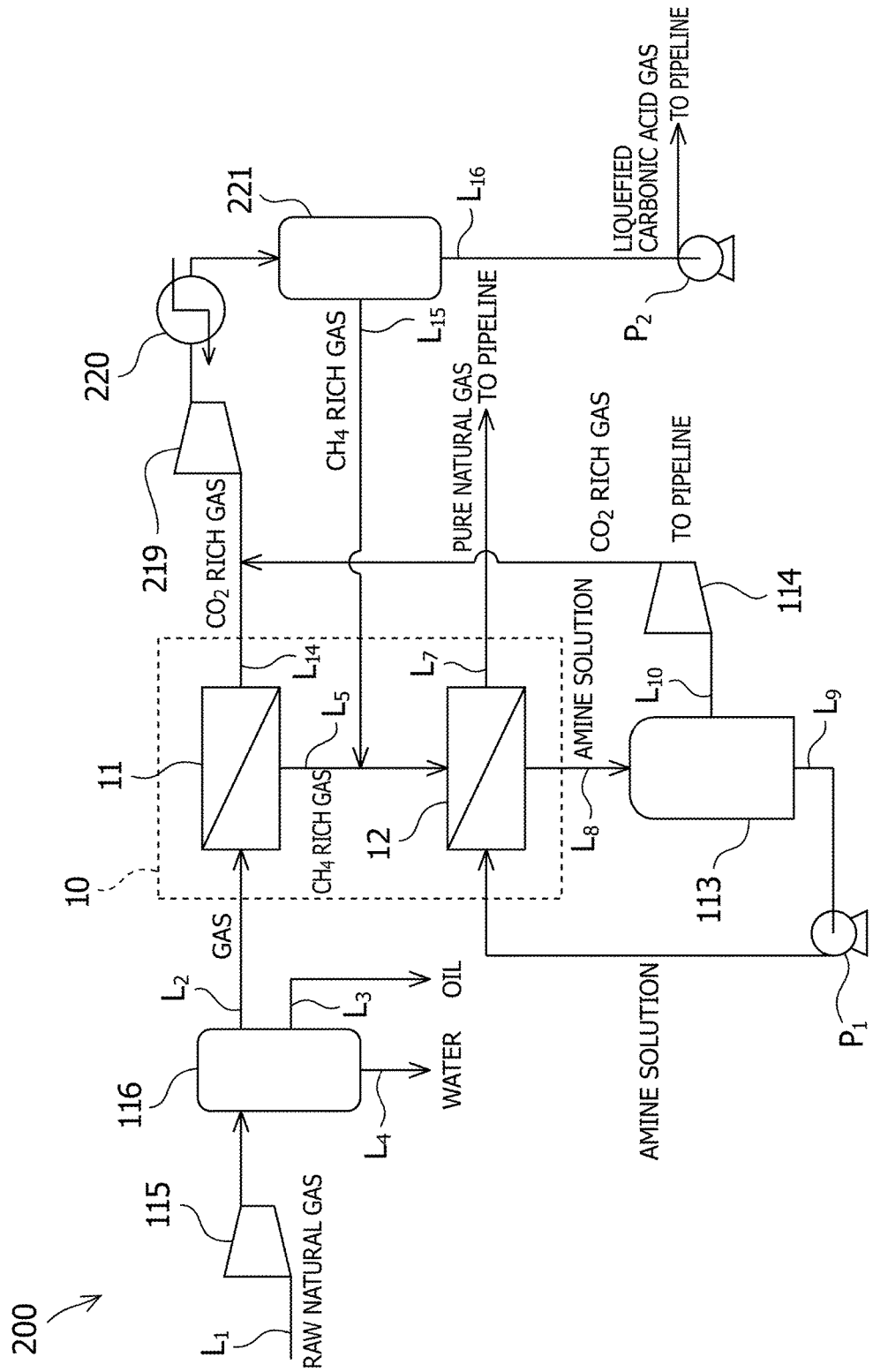
FIG. 7 is a conceptual diagram for explaining an outline for a second embodiment of a natural gas refining system according to one or more embodiments of the present invention.

As shown in FIG. 7, one or more embodiments provide for a natural gas refining system. A natural gas refining system 200 further includes a compressor 219, a cooler 220, and a gas-liquid separator 221 as compared with the system 100 of the configuration in FIG. 3.

The $CO_2$-rich gas permeated through the first separation membrane unit 11 contains $CH_4$ together with $CO_2$. For this reason, from $CO_2$-rich gas separated by the first separation membrane unit 11 and then formed into a two-phase fluid by the compressor 219 and the cooler 220 provided in a line $L_{14}$, the gas-liquid separator 221 separates $CH_4$-rich gas in a gaseous phase, and sends the $CH_4$-rich gas to the primary side of the second separation membrane unit 12 through lines $L_{15}$ and $L_5$. Meanwhile, the $CO_2$ in a liquid phase is recovered through a line $L_{16}$ and a pump $P_2$. The $CO_2$-rich gas from the compressor 114 is joined through a line $L_{10}$ into the $CO_2$-rich gas in the line $L_{14}$, which has permeated through the first separation membrane unit 11. The other constituent elements in the second embodiment are substantially the same as in the first embodiment described as shown in FIG. 3, and the constituent elements provided with the same numerals have substantially the same operations and effects. Moreover, the natural gas refining system 200 (FIG. 7) according to the present embodiment may employ the structure of the separation membrane units 11, 12 in FIG. 4, the structure of the separation membrane units 11, 12 in FIGS. 5A and 5B, or the structure including the $H_2S$ adsorption tower 117 in FIG. 6.

According to the present embodiment, it is possible to produce the same effects as in the first embodiment, and to recover the liquefied carbonic acid gas with the $CO_2$ concentration increased by the gas-liquid separator 221 from the gas permeated through the natural gas refining apparatus 10. Moreover, the gas-liquid separator 221 separates the $CH_4$-rich gas from the $CO_2$-rich gas and sends the $CH_4$-rich gas back to the natural gas refining apparatus 10, so that the $CH_4$-rich gas can be efficiently recycled.

(Modifications)

In the aforementioned embodiments of the natural gas refining apparatus and system, shown is an example of the natural gas refining apparatus 10 which has the structure including the first separation membrane unit 11 and the second separation membrane unit 12. The present invention is not limited to this structure. As described with reference to FIG. 2A, it is possible to obtain pure natural gas with required product quality only by using the first separation membrane unit 11. Hence, in some cases, only the first separation membrane unit 11 may be incorporated as a natural gas refining apparatus into a system depending on a required purpose or usage.

Figure 8:
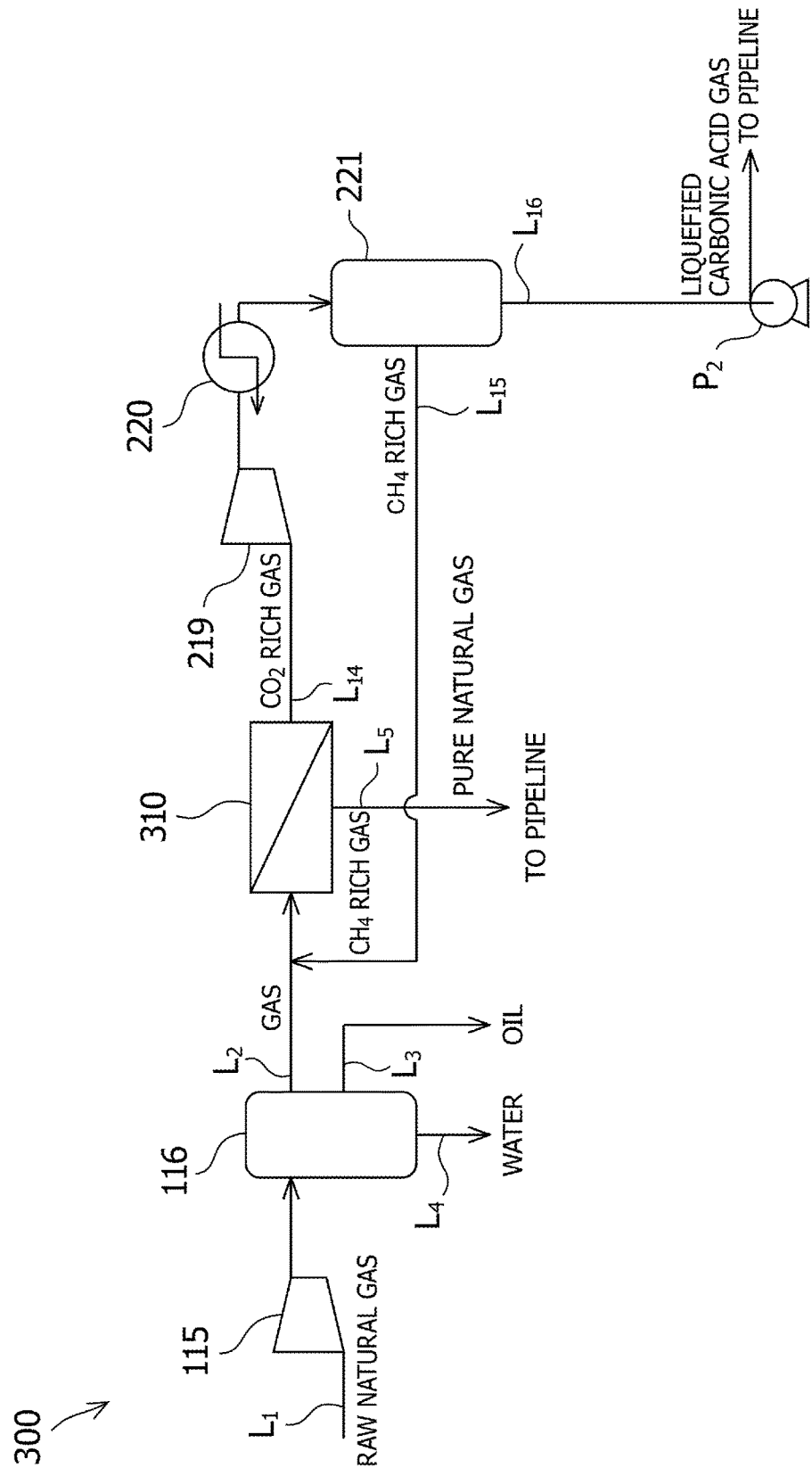
FIG. 8 is a conceptual diagram for explaining an outline for another embodiment of a natural gas refining apparatus and a natural gas refining system according to one or more embodiments of the present invention.

As one example of such a system, FIG. 8 shows a natural gas refining system 300 in which a natural gas refining apparatus 310 including only the first separation membrane unit 11 is incorporated. The system obtains the passing gas flowing from the natural gas refining apparatus 310 as pure natural gas with product quality, and meanwhile compresses and cools the permeate gas through the separation membrane to separate the permeate gas into liquid and gas, thereby recovering the liquefied carbonic acid gas while recycling the $CH_4$-rich gas by sending the $CH_4$-rich gas back to the natural gas refining apparatus 310. The system as shown in FIG. 8 is capable of obtaining pure natural gas with product quality without using an absorption method using an absorption liquid, and therefore is advantageous in off-shore plants where use of the absorption liquid is difficult. Further, as compared with a natural gas refining apparatus or system using, for example, the Selexol process (absorption by cold ethylene glycol), the system as shown in FIG. 8 can reduce energy consumption because a depressurizing operation for regenerating the absorbent is unnecessary, and can obtain pure natural gas with product quality.

Moreover, in the aforementioned embodiments of the natural gas refining apparatus and system, shown is an example of the structure in which the natural gas refining system employs the two or more first separation membrane units 11 and second separation membrane units 12 arranged in series and/or in parallel. The present invention is not limited to this structure. As described with reference to FIG. 2A, only using the first separation membrane unit 11, the natural gas refining apparatus is capable of reducing the membrane area and obtaining pure natural gas with product quality. Thus, only first separation membrane units 11 arranged in series and/or in parallel may be applied to a natural gas refining system according to one or more embodiments of the present invention, as a matter of course.

A natural gas refining apparatus and system according to one or more embodiments of the present invention can be made compact in structure and thereby reduce the energy consumption. In addition, the apparatus and system are capable of purifying natural gas with favorable quality.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST

1: vessel, 2a: upper channel, 2b: lower channel, 3: separation membrane, 4a, 4b: pipe plate, 5: inner chamber, 10, 310: natural gas refining apparatus, 11: first separation membrane unit, 11a, 117a, 117b, 117c: on-off valve, 12: second separation membrane unit, 100, 200, 300: natural gas refining system, 113: regeneration tower, 114, 115, 219: compressor, 116, 221: gas-liquid separator, 117: $H_2$ adsorption tower, 220: cooler

The invention claimed is:

1. A natural gas refining apparatus comprising:
a first separation membrane unit including a first separation membrane; and
a second separation membrane unit provided in a subsequent stage of the first separation membrane unit, wherein
the second separation membrane unit includes a second separation membrane that allows an amine solution to circulate through the second separation membrane unit,
the natural gas refining apparatus refines raw natural gas containing $CO_2$ by passing the raw natural gas through the first and second separation membrane units, separating $CO_2$-rich gas with the first separation membrane, and absorbing $CO_2$ with the amine solution circulating through the second separation membrane unit; and
a gas-liquid separator that recovers, as liquefied carbonic acid gas, the $CO_2$-rich gas permeated through the first separation membrane unit, and separates $CH_4$-rich gas from the $CO_2$-rich gas to send the $CH_4$-rich gas back to a preceding stage of the second separation membrane unit.

2. The natural gas refining apparatus according to claim 1, wherein the first and second separation membrane units each have a $CO_2/CH_4$ selectivity of 100 or more, and a permeation coefficient value of $1.0 \times 10^{-3}$ Ncc/(cm$^2$·s·cmHg) or more, with respect to $CO_2$.

3. A natural gas refining system comprising:
the natural gas refining apparatus according to claim 1; and
a regeneration tower that separates and recovers $CO_2$ from the amine solution after circulating through the second separation membrane unit to regenerate the $CO_2$, and sends the recovered $CO_2$ to the $CO_2$-rich gas separated with the first separation membrane.

4. The natural gas refining system according to claim 3, further comprising a $H_2S$ adsorption tower provided in a preceding stage of the natural gas refining apparatus that adsorbs $H_2S$ in the raw natural gas and desorbs and recovers the adsorbed $H_2S$.

* * * * *